United States Patent [19]

Empson

[11] 4,446,734

[45] May 8, 1984

[54] MOTOR DRIVEN EXCITER

[75] Inventor: Kenneth G. Empson, Montgomery, Ill.

[73] Assignee: Southern Pacific Transportation Company, San Francisco, Calif.

[21] Appl. No.: 337,984

[22] Filed: Jan. 8, 1982

[51] Int. Cl.³ .................... B06B 1/12; G01N 29/04
[52] U.S. Cl. ........................... 73/586; 73/584; 73/593; 73/666; 73/672; 173/123
[58] Field of Search .................. 73/579, 584, 586, 593, 73/666, 667, 672; 173/123

[56] References Cited

U.S. PATENT DOCUMENTS

| 2,252,017 | 8/1941 | McCrery | 173/123 |
| 2,342,601 | 2/1944 | Pyle | 173/123 |
| 3,097,523 | 7/1963 | Diamond et al. | 73/584 |
| 3,580,056 | 5/1971 | Warner | 73/579 |
| 4,050,292 | 9/1977 | Block | 73/593 |
| 4,177,798 | 12/1979 | Leveque et al. | 73/584 |
| 4,342,229 | 8/1982 | Massa | 73/579 |

FOREIGN PATENT DOCUMENTS 151504 10/1981 German Democratic Rep. ... 73/579

Primary Examiner—Howard A. Birmiel
Attorney, Agent, or Firm—Freilich, Hornbaker, Rosen & Fernandez

[57] ABSTRACT

A hammer-type device is driven by a cam and spring arrangement in reciprocating motion to strike a moving train wheel for producing vibrations therein which are used to detect defects in the wheel.

6 Claims, 3 Drawing Figures

MOTOR DRIVEN EXCITER

FIELD OF THE INVENTION

The present invention generally relates to train wheel testing devices and, more particularly, to an exciter for striking wheels of a moving train to produce sound waves which are used to detect defects in the wheels.

BACKGROUND OF THE INVENTION

The use of sound waves to test train wheels in order to detect defects, such as cracks, is well known. Typically a hammer-like element, analogous to a bell clapper, is used to strike the moving train wheel. As a result of the impact, sound waves, hereafter simply referred to as sound, is produced. Pick up devices pick up the sound and convert it to electrical signals, which are then transmitted to an analysing device e.g. a computer.

Various devices, often referred to as exciters, are presently used to strike train wheels. One of these devices is of the treadle type. The passing train wheel mechanically activates a treadle which then drives the hammer head to strike the wheel. The treadle type exciter is not very reliable. It is only useable with a very slow moving train up to 1 or 2 miles per hour (mph) and the impact force which it produces is not constant, resulting in difficulties in the analysis of the produced sounds. Another known exciter employs a solenoid to drive a hammer. This exciter also suffers from significant limitations. It is useable with trains moving at not more than about 10 mph. Also, it requires high electrical current, on the order of 100 amps to drive the hammer.

OBJECTS AND SUMMARY OF THE INVENTION

It is a primary object of the invention to provide a new improved exciter for stiking a train wheel to generate sound.

Another object of the invention is to provide a reliable exciter which is operable satisfactorily with wheels moving at a speed of up to 20 mph.

A further object of the invention is to provide an exciter wehich strikes moving train wheels at a uniform substantially constant force, and which requires less electrical power than that required by prior art exciters.

These and other objects of the invention are achieved by providing an exciter in which the hammer motion in a direction perpendicular to the direction of movement of the wheel to be stricken is controlled by one complete revolution of a cam, which is mounted on a shaft. The hammer comprises an elongated handle with a hammer head, preferrably ball shaped at the handle's front end. The handle is pivotally supported above the exciter base plate by a pair of pivoting arms, so that the handle can be moved toward and away from the wheel. One of these arms has a cam follower attached to it.

Iniatially the handle is urged by the cam away from the train track. When a wheel is known to be present at the exciter location a control signal is received which causes the shaft and the cam which is mounted thereon to make one complete revolution. As the cam moves from the initial position, at which the handle is biased away from the track, due to the cam shape, it acts as a trigger. Thus, the handle, under the biasing force of a biasing spring, accelerates toward the wheel, until the head strikes the wheel. The continually rotating cam then urges the handle away from the wheel until the full revolution is completed at which point the cam's rotation stops, and the exciter is in position to respond to a subsequent control signal.

The novel features that are considered characteristic of this invention are set forth with particularity in the appended claims. The invention will best be understood from the following description when read in connection with the accompanying drawings.

DETAILED DESCRIPTION OF THE DRAWINGS

Figure 1:
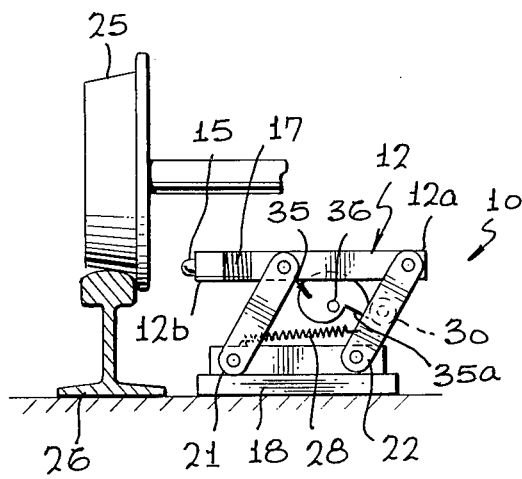
FIGS. 1 and 2 are side views of the hammer assembly in two different positions, useful in explaining the invention.

Attention is first directed to FIGS. 1 and 2 in connection with which, the novel aspects of the exciter of the present invention will be described. The exciter 10 includes a hammer unit, consisting of an elongated hammer 12 with a hammer head 15, which is preferably ball shaped, but may be shaped other than as a ball. In a preferred embodiment the hammer 12 consists of a rear member 12a and a front member 12b which supports the head 15. The members 12a and 12b are held together by a coil spring flex joint 17 to enable the front member 12b with the head 15 supported thereby to flex or pivot with respect to rear member 12a.

The hammer, or handle 12 is pivotably supported above the base 18 of the exciter by a pair of pivoting arms 21 and 22 to facilitate the horizontal movement of the handle toward and away from a train wheel 25 shown riding on a track 26. Also included is a biasing spring 28 which is shown connected to arm 22. Its function is to apply a biasing force to arm 22 and through it to the handle 12 to drive the latter toward the wheel on the track, as represented in FIG. 2 by arrow 29.

The arm 22 supports a cam follower 30, which due to the biasing force provided by spring 28 maintains contact i.e. follows, a cam 35 which is mounted on a rotatable shaft 36. As will be shown hereafter in detail the shaft 36 is coupled to a driving mechanism which is responsive to control signals succesively received from an external unit, such as a trackside computer. When a control signal is received the driving mechanism rotates the shaft 36 and the cam 35 which is supported thereby one complete revolution.

Prior to the start of one revolution the cam is in a position as shown in FIG. 1. In this position, referred to as the initial position, due to the cam's shape in spite of the biasing force of spring 28 the cam follower is urged in a direction (rightward) so that the arm 22 pivots the handle 12 fartherest from the wheel. The cam is shaped with a gradually lifting portion extending around most of the cam circumference, and a release portion 35a. As soon as a control signal is received and rotation starts away from the initial position 1 then due to the cam's release portion 35a, the follower 30 is effectively released by the cam. Thus, the baising force of spring 28 takes over, driving the handle toward the wheel. The biasing force is quite strong so that when the hammer head 15 strikes the wheel, as shown in FIG. 2, a strong enough sound is produced. The spring 28 has sufficient resiliency so that even after a very large number of cycles of operation the velocity of the head at the time of striking successive wheels is substantially the same. i.e. constant. This is most important to simplify the analysis of the sounds to distinguish between defective and satisfactory wheels.

The cam is also shaped so that as soon as the head 15 strikes the wheel on appropriate sound is produced. The head is retracted and thus disengaged from the moving wheel. At the end of the complete revolution the hammer returns to the initial position, as shown in FIG. 1.

The driving mechanism, used to apply the one revolution rotational force to shaft 36 and cam 35 is chosen to turn the shaft very fast. Thus the actual time during which the head 15 is in contact with the wheel is extremely short. In one embodiment the duration of one revolution, representing an entire hammer cycle time is on the order of 80 ms. During 80 ms even at a speed of 30 mph a wheel's travel is only about 2.5 feet or 30 inches. However the time of actual contact of the hammerhead with the wheel is only a very small portion of an entire cycle. Assuming that to be 1/30 of a cycle, the wheel moves about one inch when the hammer head is in actual contact therewith.

Figure 2:
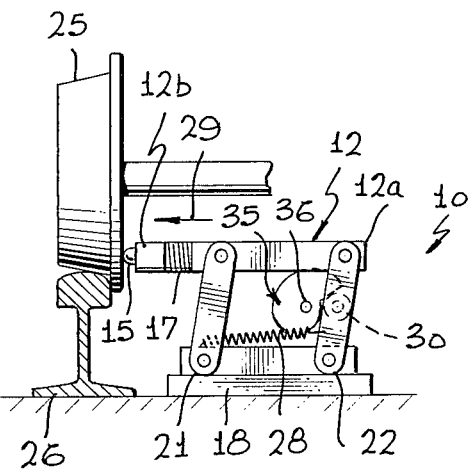
Figure 3:
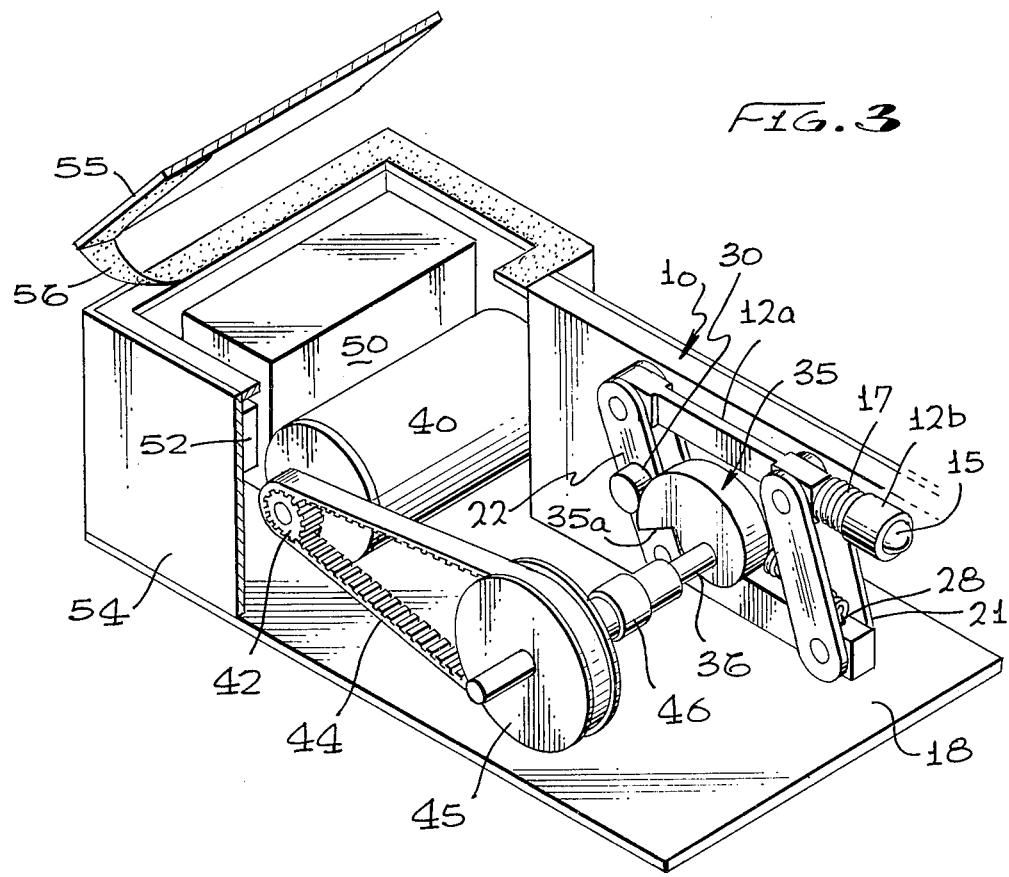
FIG. 3 is perspective of an exciter in accordance with the present invention.

To prevent any damage to the hammer as a result of any linear motion of the wheel during the contact period, the hammer head 15 is ball shaped as shown in FIGS. 1 and 2 so that it only makes a point contact with the moving wheel. Furthermore by incorporating the coil spring flex joint 17 the handle member 12b with hammerhead 15 are capable of flexing with respect to the rest of the hammer assembly. Thus any drag of the hammerhead 15 by a moving wheel is taken up by the flex joint 17 to prevent permanent damage to the assembly 10. As shown in FIG. 3, to which reference is now made, if desired the ball shaped hammer head 15 may be rotatably supported in handle member 12b to further reduce any damage to the hammer head by any protrusions on the moving wheel, when the two are in contact with one another.

Various means may be used to drive the shaft 36 on which the cam 35 is supported one complete revolution in response to the receipt of each control signal. One arrangement for rotating the shaft 36 one revolution per control signal is shown in FIG. 3. Therein numeral 40 designates a motor which by means of a shaft mounted gear 42, a belt 44 and a pulley 45 drives shaft 36 through an incremental clutch 46. Shown associated with the motor 40 are a power source 50 and a motor controller 52 in a housing 54 with a lid 55 and a protective gasket 56. The power source 50 may be of the DC type, example a battery, or an external source of conventional AC voltage.

In operation when a wheel is at a given distance from the exciter 10, the motor is turned on. However, shaft 36 does not rotate since the incremental clutch 46 is disengaged. Then, when sidetrack instruments sense that a wheel faces the exciter 10, a control signal is applied to the incremental clutch 46, and energizes it. In the particular clutch, incorporated in one embodiment, when the control signal is received a clutch solenoid is energized which releases a pawl, thereby enabling the shaft 36 attached to cam 35 to rotate. At the end of one complete revolution the shaft rotation stops by the clutch's pawl at the cam highest position shown in FIG. 1, i.e. at the initial position, until a second control signal is received and a second rotation cycle takes place.

Incremental clutches are well known in the art. In a particular embodiment, an incremental clutch available from Warner Electric Brake and Clutch Company of Beloit Wisconsin 53511, Catalog No. CB-5 was used.

Although particular embodiments of the invention have been described and illustrated herein, it is recognized that modifications and variations may readily occur to those skilled in the art. Consequently, it is intended that the claims be interpreted to cover such modifications and equivalents.

What is claimed is:

1. Apparatus for striking a moving train wheel, comprising:
    a hammer unit which includes a hammer, means for supporting said hammer in movement toward and away from the path of the moving train wheel, a spring which urges said hammer towards the path of the wheel when the hammer is held away from the path of the wheel, and means for moving said hammer away from the path of the wheel in opposition to the force of the spring and for releasing the hammer to allow its movement by said spring against a moving train wheel;
    said hammer including front and rear members, said spring and moving means coupled to said rear member, and said front member lying closest to said train wheel path and having a head that strikes a train wheel, at least said head moveable, relative to said rear member, by a limited distance perpendicular to hammer movement toward and away from said wheel path.

2. The apparatus described in claim 1 wherein:
    said hammer includes a spring connecting said front and rear hammer members, to permit deflection of said front member.

3. Apparatus for only occasionally striking a moving train wheel, comprising:
    a hammer unit which includes a hammer, means for supporting said hammer in movement toward and away from the path of the moving train wheel, a spring which urges said hammer towards the path of the wheel when the hammer is held away from the path of the wheel, and means for moving said hammer away from the path of the wheel in opposition to the force of the spring and for releasing the hammer to allow its movement by said spring against a moving train wheel;
    said means for moving said hammer includes a cam follower coupled to said hammer, a rotatable cam shaft and a cam mounted on said shaft and coupled to said cam follower, said cam having a gradual lifting portion that gradually moves said hammer away from the wheel path during most of one revolution of the cam shaft, said lifting portion having a highest position and said cam having a release portion immediately following said highest position that suddenly releases said cam follower so it can move toward the beginning of said gradual lifting portion;
    said means for moving also including an intermittently operated motor and clutch means for coupling said motor to said cam shaft to stop rotation of said cam shaft when said highest portion thereof engages said follower.

4. The apparatus described in claim 3 wherein:
    said hammer has a ball-like front end.

5. The apparatus described in claim 3 wherein:
    said means for supporting said hammer includes a base mounted to the ground and a pair of substantially parallel arms having inner ends pivotally connected to said base and outer ends pivotally connected to spaced locations on said hammer; and said cam follower is mounted on one of said arms.

6. Apparatus for striking a moving train wheel, comprising:

a hammer unit which includes a hammer, means for supporting said hammer in primarily horizontal movement toward and away from the path of the moving train wheel, a spring which urges said hammer towards the path of the wheel when the hammer is held away from the path of the wheel, and means for moving said hammer away from the path of the wheel in opposition to the force of the spring and for releasing the hammer to allow its movement by said spring against a moving train wheel;

said means for supporting said hammer including a base mounted to the ground and a pair of substantially parallel arms having inner ends pivotally connected to said base and outer ends pivotally connected to spaced locations on said hammer.

* * * * *